United States Patent [19]

Cutchens et al.

[11] Patent Number: 4,491,673

[45] **Date of Patent: * Jan. 1, 1985**

[54] PRODUCTION AND SEPARATION OF AMINES

[75] Inventors: Charles E. Cutchens; Marion J. Mathews, III; Mark S. Sowell, III, all of Pensacola, Fla.

[73] Assignee: Monsanto Company, St. Louis, Mo.

[ * ] Notice: The portion of the term of this patent subsequent to Jul. 26, 2000 has been disclaimed.

[21] Appl. No.: 369,443

[22] Filed: Apr. 19, 1982

[51] Int. Cl.[3] ....................... C07C 87/14; C07C 87/16

[52] U.S. Cl. .................................... 564/492; 564/491; 564/493

[58] Field of Search ............... 564/492, 491, 490, 498, 564/497

[56] References Cited

U.S. PATENT DOCUMENTS

| | | | |
|---|---|---|---|
| 3,821,305 | 6/1974 | Bartalini et al. | 260/583 K |
| 4,053,516 | 10/1977 | Hammerstrom et al. | 260/585 A |
| 4,283,254 | 8/1981 | Binau | 564/497 |
| 4,359,585 | 11/1982 | Campbell et al. | 564/498 |
| 4,375,003 | 2/1983 | Allain et al. | 564/491 |
| 4,395,573 | 7/1983 | Cutchens | 564/492 |
| 4,429,159 | 1/1984 | Cutchens et al. | 564/490 |

*Primary Examiner*—William R. Dixon, Jr.
*Assistant Examiner*—Margaret B. Medley
*Attorney, Agent, or Firm*—Thomas Y. Awalt, Jr.

[57] ABSTRACT

This invention provides for the separation of the contents of the process discharge stream of reaction in which an amine is produced from a nitrile. An inorganic base having a concentration greater than 40 weight percent is introduced into the process discharge stream which is decanted, purged, flashed, and a portion thereof recycled.

6 Claims, 1 Drawing Figure

11
3
4
12
13
15
18
19
5
16
17
1
2
25
6
20
14
23
7
8
21
9
24
22
10

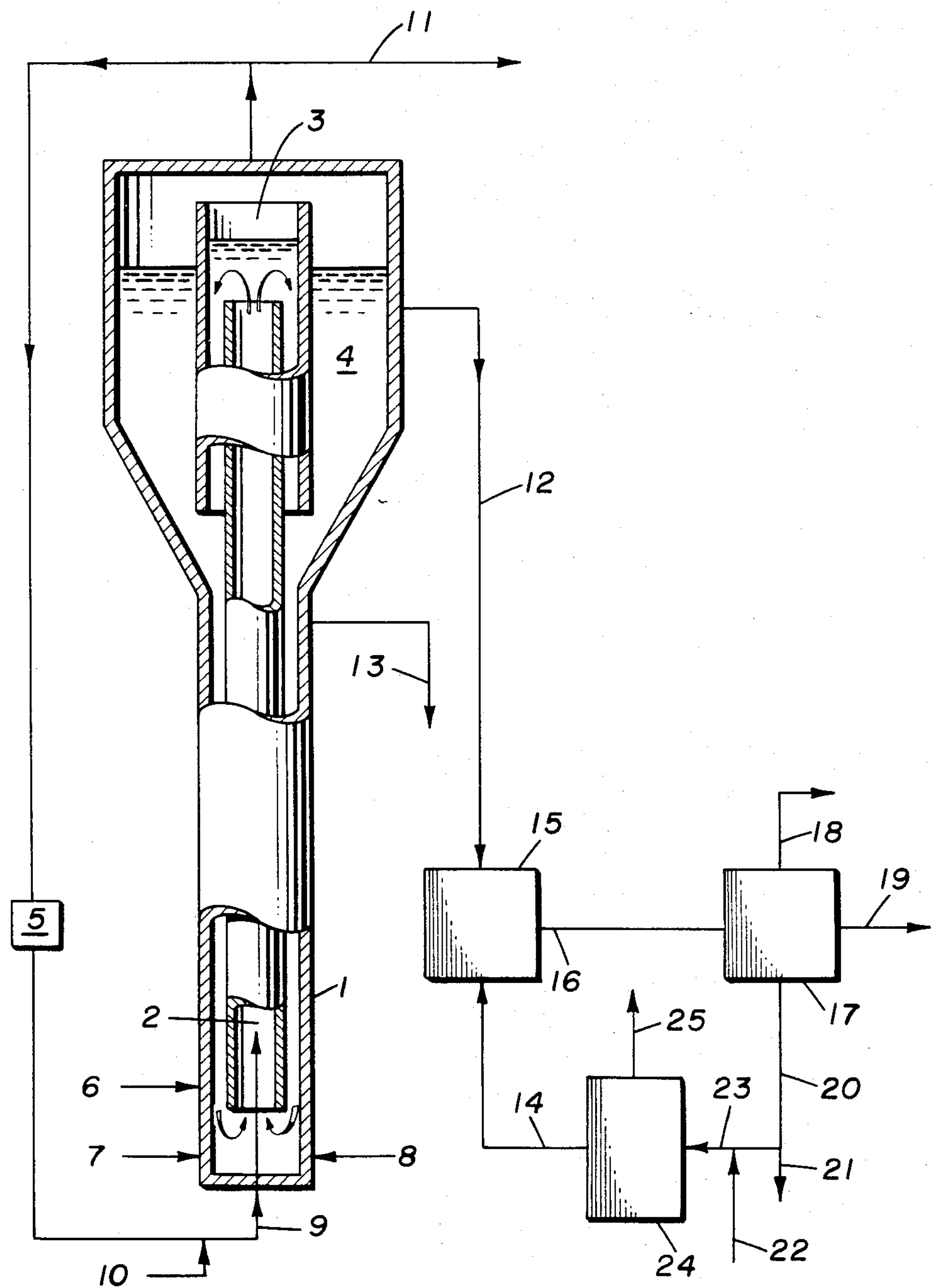
11
3
4
12
13
15
18
19
5
16
17
2
1
25
6
23
20
14
7
8
21
9
22
10
24

PRODUCTION AND SEPARATION OF AMINES

FIELD OF THE INVENTION

The invention relates to a process for the production of an amine such as hexamethylenediamine from a nitrile such as adiponitrile where the nitrile is hydrogenated under pressure in the presence of a Raney nickel catalyst, the reaction being conducted in a reactor from which is discharged a product stream containing both the amine and Raney nickel catalyst.

BACKGROUND OF THE INVENTION

It is well known that amines such as hexamethylenediamine can be produced by the catalytic hydrogenation of nitriles such as adiponitrile in the presence of Raney catalysts.

One such process is described in U.S. Pat. No. 3,821,305, in which hydrogenation is conducted in liquid phase at pressures of from 20–50 atmospheres and temperatures of 60°–100° C. in the presence of finely divided Raney catalyst and an inorganic base. Hydrogen and adiponitrile are fed into a liquid reaction medium consisting of hexamethylenediamine, water, the inorganic base, and the catalyst, in which medium the content of base is maintained in the range of 0.2–12 moles per kilogram of catalyst, while the content of water is maintained in the range of 2–130 moles per mole of the base.

The process discharge stream in the above described process contains both residual Raney nickel catalyst and the product hexamethylenediamine, from which it is desirable to recover substantially pure hexamethylenediamine by distillation.

In order to passify the residual Raney nickel catalyst so as to prevent decomposition of the product hexamethylenediamine it is known to charge to the product discharge stream an inorganic base. The utilization of this inorganic base to assist in the separation of the product hexamethylenediamine would constitute a significant improvement in the art and is an object of this invention.

SUMMARY OF THE INVENTION

Briefly, the invention is an improvement in a process for the purification of an amine such as hexamethylenediamine produced from a nitrile such as adiponitrile where the nitrile is hydrogenated under pressure in the presence of a Raney nickel catalyst continuously in a reactor thereby to produce an amine which is discharged in a stream from which is recovered both hexamethylenediamine and residual Raney nickel catalyst. An inorganic base is charged to the process discharge stream in order to passify the Raney nickel catalyst and prevent catalytic decomposition of the amine. According to this invention, an inorganic base feed is mixed with the process discharge stream to form a separable two phase mixture having a first phase comprising the product amine and a second phase comprising an aqueous solution of the inorganic base having more than 40% by weight inorganic base. The separable mixture is fed to a decanter where, in the course of decantation, hexamethylenediamine is removed from the top and the Raney nickel catalyst is purged from an interface between the amine and the inorganic base. A portion of the second phase (removed) is purged in order to remove aluminum compounds therein. To the remainder of the second phase (removed) fresh inorganic base is added and water is flashed off as required to form the inorganic base feed having more than 40% weight percent inorganic base.

DETAILED DESCRIPTION OF THE INVENTION

While the invention is applicable to the purification process for the production of any amine produced from a nitrile in which residual Raney nickel catalyst is present, the invention will be described in the context of a preferred process for such production.

The process for the production of the hexamethylenediamine is preferably carried out in the pressures of 20–50 atmospheres in temperatures of 60°14 100° C., by feeding molecular hydrogen and adiponitrile into a liquid reaction medium containing, along with the hexamethylenediamine produced, water, sodium hydroxide and a finely divided Raney catalyst dispersed in the liquid components of the reaction medium. The catalyst, which may be Raney nickel, or Raney nickel containing small amounts of other metals such as chromium, loses all or most of its activity during hydrogenation. In order to maintain a given level of catalytic activity with the catalytic mass, it is necessary for the catalyst in the reaction medium to be gradually replaced. This replacement is effected by feeding fresh catalyst to the reaction vessel and removing a quantity of reaction medium which contains an amount of catalyst equal to that supplied. The feed catalyst may consist of a mixture of fresh catalyst and of recycled catalyst. Recycled catalyst is catalyst that has been washed prior to re-use.

The reaction medium preferably contains:

(1) a quantity of catalyst in excess of 1 part, by weight, per 100 parts of liquid reaction medium (hexamethylenediamine, water and sodium hydroxide), the upper limit depending solely on the fluidity of the reaction medium; the preferred range is from 3 to 35 parts per 100 parts by weight of the liquid reaction medium;

(2) a quantity of sodium hydroxide in the range of 0.2 to 12 moles per kilogram of catalyst and preferably between 1 and 3 moles per kilogram of catalyst;

(3) a quantity of water in the range of 2 to 130 moles per mole of sodium hydroxide and preferably between 7 and 70 moles per mole of sodium hydroxide.

Substantially similar results in the production of the amine can be obtained by using, instead of sodium hydroxide, a hydroxide of any other of the alkali metals. Throughout the following description, however, reference will be made to the preferred sodium hydroxide.

The liquid part of the reaction medium, under the starting conditions already specified, and within the preferred range of ration of water to sodium hydroxide, consists of an aqueous solution of sodium hydroxide whose concentration is in the range of 25 to 40% percent by weight. The other phase consists of hexamethylenediamine containing water and small amounts of sodium hydroxide. The aqueous solution of sodium hydroxide, which is the heavier phase, contains most of the catalyst.

The equipment for continuous operation of the process is of conventional type.

An example of this, which is not limitive of the invention, is shown in the accompanying drawing.

The equipment consists essentially of a vertical tubular reaction vessel, 1, provided inside with an injection device, 2, such as to promote the agitation of the reaction medium resulting from hydrogen flow, and at the top with containers, 3 and 4, which enable the separation of the gas from the liquid and the drawing off from the reaction vessel of a hydrogenated product having a low content of catalyst thus making it possible to maintain in the reaction vessel relatively high concentrations of catalyst—for example, 10 and 20 parts of catalyst per 100 parts by weight of liquid reaction medium.

The equipment also includes a gas re-cycling pump, 5 and pipes for feeding the reaction vessel with adiponitrile 6, aqueous solution of sodium hydroxide 7, catalyst 8, and hydrogen 9. The hydrogen consumed is replaced by feeding fresh hydrogen through pipe 10.

Part of the gas is vented through pipe 11, the purpose of this release being to maintain the hydrogen content in the re-cycled gas above a given value.

Hexamethylenediamine is discharged through pipe 12.

Pipe 13 is used for removing an amount of reaction medium whose catalyst content is equivalent to the amount supplied through pipe 7. In this way, the concentration of catalyst in the reaction medium remains constant.

The inorganic base may be introduced to the product discharge stream at any convenient point.

According to the preferred embodiment the inorganic base is charged to mixer 15 through pipe 14. The product discharge stream is transmitted through pipe 12 to mixer 15 from which it is transmitted through pipe 16 to decanter 17. Crude hexamethylenediamine upper phase is decanted off through pipe 18. A layer of catalyst is removed at pipe 19. From the decanter the inorganic base (lower phase) is removed through pipe 20 and a portion may be purged through pipe 21. Equilibrium between the upper and lower phases can be controlled by fresh addition of inorganic base through pipe 22. Flasher 24 is used to raise the concentration of the inorganic base as required to maintain the over 40% weight percent level. Water is flashed off through pipe 25 and the concentrated inorganic base is recycled to mixer 15 through pipe 14. As indicated above if the concentration of inorganic base in decanter 17 decreases excessively the adjustment may involve (1) increasing the amount of water being flashed off in flasher 24, (2) the addition of concentrated inorganic base through pipe 22, (3) purging through pipe 21 or any combination thereof. Concentrations of inorganic base must be more than 40% by weight in stream 14 in order to drive down the concentrations of both base and water in the upper phase. Concentrations well in excess of 40% may be employed up to 70% but at higher concentrations there may be a problem created by freezing of the recycled lower phase if temperatures are allowed to run as low as about 65.5° C. (150° F.) or below, for concentrations of 70%, while perhaps workable, should be avoided so as to prevent freezing.

As will be seen in the examples, mixing temperatures of the order of 70°-90° C. have been demonstrated to be satisfactory.

EXAMPLES

To a process discharge stream 12 of the type show in the FIGURE was charged sodium hydroxide in the amount shown, and the stream was subjected to mixing and decantation as described above, at temperature ranges shown at Table I. The effect of the flasher was simulated by control of NAOH concentration. Measurements of sodium, water and aluminum content were taken in both crude hexamethylenediamine (pipe 12) and from the decanted crude hexamethylenediamine stream (pipe 18). The results are as shown in Table I.

TABLE I

CRUDE HEXAMETHYLENEDIAMINE (CHMD) CAUSTIC WASH
CHMD (Pipe 12): 301 ppm Na, 9 ppm Al, 11.6% $H_2O$
Mixture Ratio, CHMD/Aqueous NaOh (Pipe 12/Pipe 14): 2/1 wt./wt.
Decanter 17 Settling Time: 5 minutes

| Wt. % NaOH | Temperature | Decanted CHMD (Pipe 18) | | |
|---|---|---|---|---|
| (Pipe 14) | °C. | ppm Na | ppm Al | % $H_2O$ |
| 20 | 70 | 2089 | <1 | 31.3 |
| 40 | 70 | 289 | <1 | 11.6 |
| 55 | 70 | 205 | 3 | 5.8 |
| 55 | 90 | 211 | <1 | 5.6 |
| 70 | 70 | 312 | 8 | 3.5 |

As seen from Table I, striking and unforseen reductions in water content are shown in the product when concentrations of NaOH are increased to above 40%. These reductions are accompanied by reductions in the amount of NaOH and Al compounds in the product at concentrations of NaOH up to 70%.

We claim:

1. In a process for the production of an amine from a nitrile where the nitrile is hydrogenated under pressure in the presence of a Raney nickel catalyst continuously in a reactor thereby to produce the amine which is discharged in a stream from which is recovered the amine and residual Raney nickel catalyst, where the Raney nickel catalyst is passivated by charging to the process discharge stream comprising the product amine and the Raney nickel catalyst an inorganic base, and where the product amine is subsequently separated from the Raney nickel catalyst and the inorganic base, the improvement wherein the separation is characterized by mixing an inorganic base feed with the process discharge stream to form a separable two phase mixture having a first phase comprising the product amine and a second phase comprising an aqueous solution of the inorganic base having more than 40% by weight inorganic base, decanting the separable mixture so as to remove the upper layer comprising the first phase from the lower layer comprising the second phase, purging Raney nickel catalyst at the interface of the first and second phases, purging a portion of the second phase (removed) in order to remove aluminum compounds therein, adding fresh inorganic base to and flashing off water from the second phase (removed) as required to form the inorganic base feed with a concentration more than 40 weight percent.

2. The process of claim 1 wherein the nitrile is adiponitrile and the amine is hexamethylenediamine.

3. The process of claim 1 wherein the inorganic base is sodium hydroxide.

4. The process of claim 2 which the temperature of the product stream in the decanter during decantation is in the range of 70°-90° C.

5. The process of claim 1 wherein the concentration of inorganic base in the feed is 55-70% by weight.

6. In a process for the production of hexamethylenediamine produced from adiponitrile where the adiponitrile is hydrogenated under pressure in the presence of a Raney nickel catalyst continuously in a reactor thereby to produce hexamethylenediamine which is discharged in a stream from which is removed both the hexamethylenediamine and residual Raney nickel catalyst, where the Raney nickel catalyst is passivated by charging sodium hydroxide to the process discharge stream comprising the product hexamethylenediamine and the Raney nickel catalyst, and where the product hexamethylenediamine is subsequently separated from the Raney nickel catalyst and the sodium hydroxide, the improvement wherein the separation is characterized by mixing a sodium hydroxide feed with the process discharge stream to form a separable two phase mixture having a first phase comprising the product hexamethylenediamine and a second phase comprising an aqueous solution of sodium hydroxide having more than 40% by weight sodium hydroxide, decanting the separable mixture so as to remove the first phase from the lower layer comprising the second phase, purging Raney nickel catalyst at the interface of the first and second phases, purging a portion of the second phase (removed) in order to remove aluminum compounds therein, and adding fresh sodium hydroxide and flashing off water as required to form the sodium hydroxide feed with a concentration of more than 40 weight percent.

* * * * *

UNITED STATES PATENT AND TRADEMARK OFFICE
CERTIFICATE OF CORRECTION

PATENT NO. : 4,491,673

DATED : January 1, 1985

INVENTOR(S) : Charles E. Cutchens; Marion J. Mathews, III; Mark S. Sowell, III

It is certified that error appears in the above-identified patent and that said Letters Patent are hereby corrected as shown below:

Column 2, line 14, "60°14 100°" should read --60-100°--.

Signed and Sealed this

*Thirtieth* Day of *July 1985*

[SEAL]

*Attest:*

DONALD J. QUIGG

*Attesting Officer* *Acting Commissioner of Patents and Trademarks*